(12) United States Patent
Arbiser

(10) Patent No.: US 8,822,531 B2
(45) Date of Patent: *Sep. 2, 2014

(54) HONOKIOL ANALOGS AND THEIR USE IN TREATING CANCERS

(71) Applicant: Jack L. Arbiser, Atlanta, GA (US)

(72) Inventor: Jack L. Arbiser, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/956,194

(22) Filed: Jul. 31, 2013

(65) Prior Publication Data

US 2013/0345302 A1    Dec. 26, 2013

Related U.S. Application Data

(63) Continuation of application No. 12/598,719, filed as application No. PCT/US2008/061899 on Apr. 29, 2008.

(60) Provisional application No. 60/934,322, filed on Jun. 13, 2007, provisional application No. 60/927,338, filed on May 3, 2007.

(51) Int. Cl.
*C07C 69/00* (2006.01)
*C07D 303/12* (2006.01)
*A61K 31/335* (2006.01)

(52) U.S. Cl.
USPC ............................ 514/475; 549/554; 560/141

(58) Field of Classification Search
USPC ................... 549/512, 554; 568/650; 514/475; 560/141
See application file for complete search history.

(56) References Cited

U.S. PATENT DOCUMENTS

2010/0322991 A1    12/2010    Arbiser

FOREIGN PATENT DOCUMENTS

WO        02076393 A2    10/2002
WO     2006107451 A2    10/2006

OTHER PUBLICATIONS

Marques et al., Oxidative Coupling of 4-Substituted 2-Methoxy Phenols Using Methyltributylammonium Permanganate in Dichloromethane, 1998, Tetrahedron Letters, 39, p. 943-946.*
Bai, X., et al., "Honokiol, a Small Molecular Weight Natural Product, Inhibits Angiogenesis in Vitro and Tumor Growth in Vivo", "The Journal of Biological Chemistry", Sep. 12, 2003, pp. 35501-35507, vol. 278, No. 37.
Chen, F., et al., "Honokiol: A potent chemotherapy candidate for human colorectal carcinoma", "World J. Gastroenterol.", Dec. 1, 2004, pp. 3459-3463, vol. 10, No. 23.
Shigemura, K., et al., "Honokiol, a Natural Plant Product, Inhibits the Bone Metastatic Growth of Human Prostate Cancer Cells", "Cancer", Feb. 26, 2007, pp. 1279-1289, vol. 109, No. 7.

\* cited by examiner

*Primary Examiner* — T. Victor Oh
(74) *Attorney, Agent, or Firm* — Hultquist, PLLC; David Bradin

(57) ABSTRACT

Compounds, pharmaceutical compositions including the compounds, and methods of preparation and use thereof are disclosed. The compounds are honokiol analogs. The compounds and compositions can be used to treat and/or prevent a wide variety of cancers, including drug resistant cancers. Representative honokiol analogs include diepoxide honokiol analogs. The compounds are believed to function, at least, by inhibiting angiogenesis and/or inducing apoptosis. Thus, the compounds are novel therapeutic agents for a variety of cancers.

13 Claims, 1 Drawing Sheet

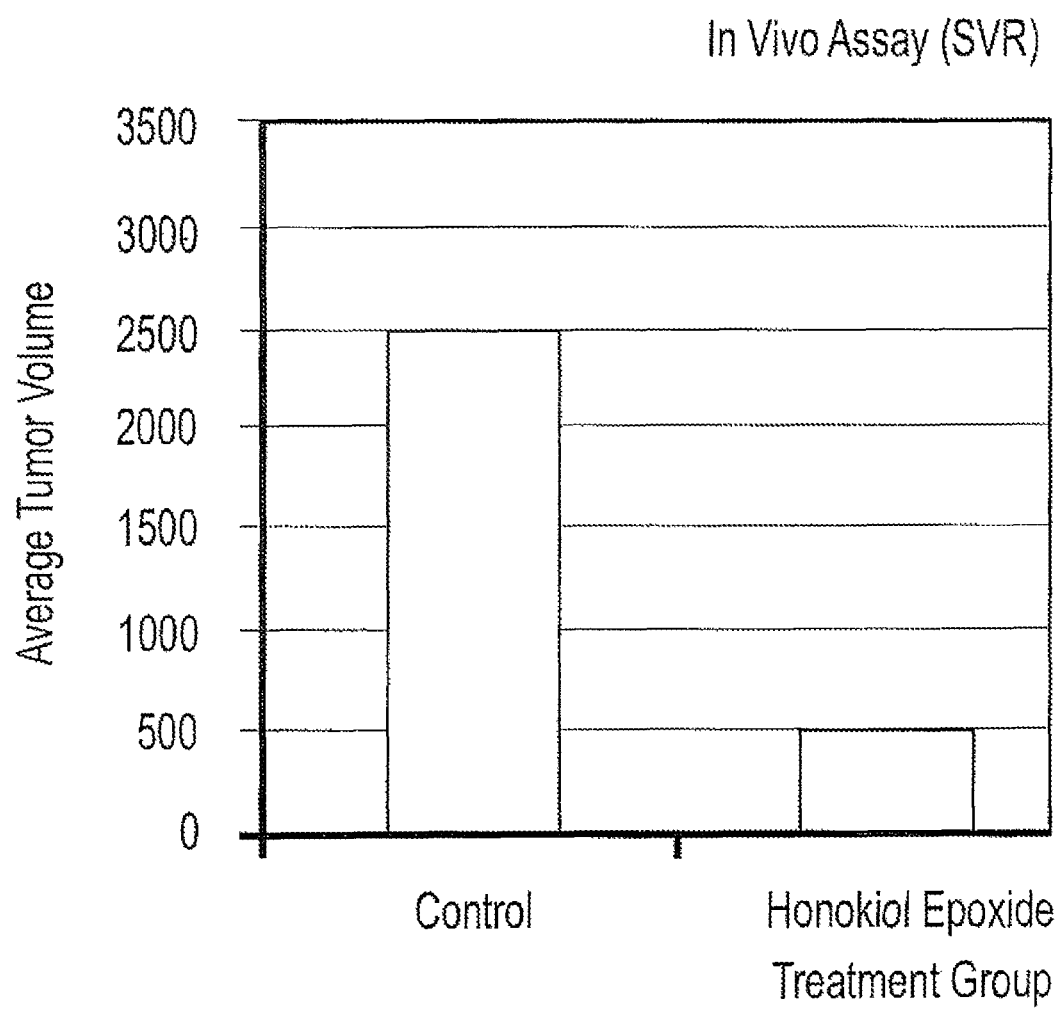

HONOKIOL ANALOGS AND THEIR USE IN TREATING CANCERS

CROSS-REFERENCE

This continuation application claims priority under 35 U.S.C. 120 to U.S. application Ser. No. 12/598,719, filed on Nov. 3, 2009, now U.S. Pat.No. 8,586,627, which in turn claims priority as the U.S. national stage entry under 35 U.S.C. 371 of PCT/US08/61899, filed Apr. 29, 2008, which in turn claims priority under 35 U.S.C. 119 to U.S. Provisional Application No. 60/934,322, filed on Jun. 13, 2007, and U.S. Provisional Application No. 60/927,338, filed on May 3, 2007. The contents of each of these applications is incorporated herein by reference for all purposes.

FIELD OF THE INVENTION

The present invention relates to novel methods and compositions for the treatment of primary and metastatic cancers. These methods and compositions use honokiol analogues. These compounds, and pharmaceutical compositions including the compounds, are particularly useful for treating primary and metastatic cancers in humans. The invention also encompasses the varying modes of administration of the therapeutic compounds or compositions.

BACKGROUND OF THE INVENTION

Natural products are a major source of small molecular weight angiogenesis inhibitors, and the transformed endothelial cell line SVR has been used to screen natural product extracts to isolate anti-angiogenesis and anti-tumor compounds (Arbiser et al., J. Biol. Chem., Vol. 278, Issue 37, 35501-35507, Sep. 12, 2003).

Aqueous extracts of *Magnolia grandiflora* exhibit potent activity in these SVR proliferation assays, and the small molecular weight compound honokiol is the active principle of magnolia extract. Honokiol has the following formula:

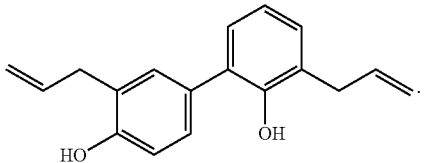 [SMILES: C=CCc1cc(-c2cccc(CC=C)c2O)ccc1O]

Honokiol exhibits potent anti-proliferative activity against SVR cells in vitro. In addition, honokiol demonstrates preferential inhibition of primary human endothelial cells compared with fibroblasts, and this inhibition was antagonized by antibodies against TNF-related apoptosis-inducing ligand. In vivo, honokiol is highly effective against angiosarcoma in nude mice. Preclinical data suggests that honokiol is a systemically available and non-toxic inhibitor of angiogenesis, and also promotes apoptosis.

There remains a need for treatment of cancer that does not have the adverse effects generally caused by non-selectivity, of conventional chemotherapeutic agents. While honokiol is an active compound, it would be advantageous to develop honokiol analogues that are even more active. The present invention provides such analogues, as well as pharmaceutical compositions including the analogues, and methods of treating cancer using the analogues.

SUMMARY OF THE INVENTION

Compounds, pharmaceutical compositions including the compounds, and methods of preparation and use thereof are disclosed.

In one embodiment, the compounds are honokiol analogs, which can be formed by reacting one or both of the double bonds in honokiol with appropriate reactants to form cyclopropane, epoxide, thiirane, or aziridine rings. A core structure similar to honokiol, where one or both of the benzene rings are replaced with a heteroaryl ring, can also be used. The linker between the aryl/heteroaryl rings and the cyclopropane, epoxide, thiirane, or aziridine rings is modified from that of honokiol, in that it can be extended from one to three carbons in length, and one of the carbons replaced with an O, S, or amine. Additionally, one or both of the hydroxyl groups on the central aryl/heteroaryl rings can be converted to an alkyl phosphate ester, or a dichloroacetate ester. Representative compounds include honokiol diepoxide and honokiol monoepoxide.

The synthesis, characterization and an evaluation of the anti-tumor potential of these honokiol analogues is also disclosed. The honokiol analogues inhibit angiogenesis and/or induce apoptosis, and thus are effective at killing growing cancer cells.

Treatment with one or more of these compounds selectively kills cancer cells, without killing healthy cells, thus providing a selective anti-cancer therapy. Most importantly, these compounds are potent against cancer cells that have become metastacized.

The pharmaceutical compositions include an effective amount of the compounds described herein, along with a pharmaceutically acceptable carrier or excipient. When employed in effective amounts, the compounds can act as a therapeutic agent to prevent and/or treat a wide variety of cancers, particularly metasticized cancers, and are believed to be both safe and effective in this role. Representative cancers that can be treated and/or prevented include melanoma, leukemia, non-small cell lung, colon, central nervous system (CNS), renal, ovarian, breast and prostate cancer.

The foregoing and other aspects of the present invention are explained in detail in the detailed description and examples set forth below.

BRIEF DESCRIPTION OF THE DRAWINGS

FIG. 1 is a chart showing the effect of honokiol diepoxide against tumor cells in vivo (average tumor volume).

DETAILED DESCRIPTION OF THE INVENTION

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched alkyl radicals including $C_{1-8}$, preferably $C_1$-$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

I. Compounds

The compounds are honokiol analogs, prodrugs or metabolites of these compounds, and pharmaceutically acceptable salts thereof, wherein one or both of the double bonds in honokiol has been replaced with a cyclopropane, epoxide, thiirane, or aziridine moiety, optionally along with other structural modifications and optional substitutions.

In one embodiment, the compounds have the following formula:

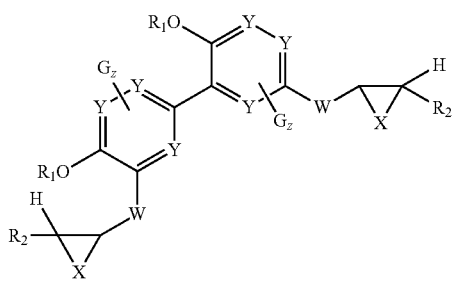

wherein:

W is $(CHR^2)n$, $O—(CHR^2)n$, $S—(CHR^2)n$, or $NR^2—(CHR^2)n$, optionally substituted with halogens, such as fluorine (i.e., $(CF_2)n$ and the like), X is O, S, or $NR^2$, Y is N or C bonded to a substituent, G, $R^1$ is H, alkyl phosphate, dichloroacetate, trifluoromethyl, or valproate, $R^2$ is H, alkyl, aryl, arylalkyl, or alkylaryl, and when bonded to carbon, halo, such as fluoro, n is an integer from 1-4, Representative substituents, G, include $C_{1-6}$ alkyl (including cycloalkyl), alkenyl, heterocyclyl, aryl, heteroaryl, halo (e.g., F, Cl, Br, or I), —OR, —$NR^3R^4$, —$CF_3$, —CN, —$NO_2$, —$C_2R^3$, —$SR^3$, —$N_3$, —C(=O)$NR^3R^4$, —$NR^3$C(=O)$R^3$, —C(=O)$R^3$, —C(=O)$OR^3$, —OC(=O)$R^3$, —OC(=O)$NR^3R^4$, —$NR^3$C(=O)$OR^3$, —$SO_2R^3$, —$SO_2NR^3R^4$, and —$NR^3SO_2R^3$, where $R^3$ and $R^4$ are individually hydrogen, $C_{1-6}$ alkyl, cycloalkyl, heterocyclyl, aryl, or arylalkyl, (such as benzyl);

z is an integer of from 0-3, but in any case cannot exceed the number of carbon atoms in the ring, one or both of the aryl rings can be replaced with thiophene, pyrrole, or furan, and one of the three membered rings can be replaced with a double bond (i.e., X represents a bond between the two carbons to which it is attached).

In one embodiment, a fluoro moiety is present ortho to one or both $OR^1$ moieties. In one aspect of this embodiment, each Y is CF.

In another embodiment, the compounds have the following formula:

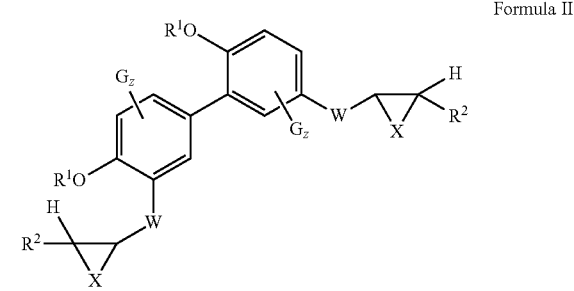

Formula II wherein W, X, $R^2$, $R^2$, G n and z are as defined above, and wherein one of the three membered rings can be replaced with a double bond.

In still another embodiment, the compounds have the following formula:

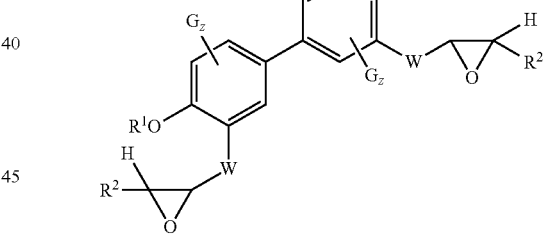

Wherein W, R1 and R2 are as defined above, and wherein one of the epoxide rings can be replaced with a double bond.

Representative individual compounds include the following:

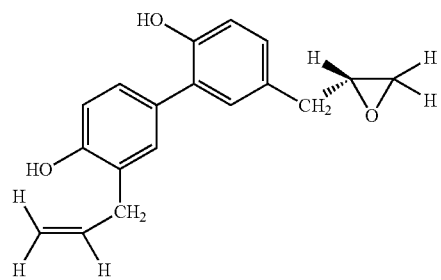

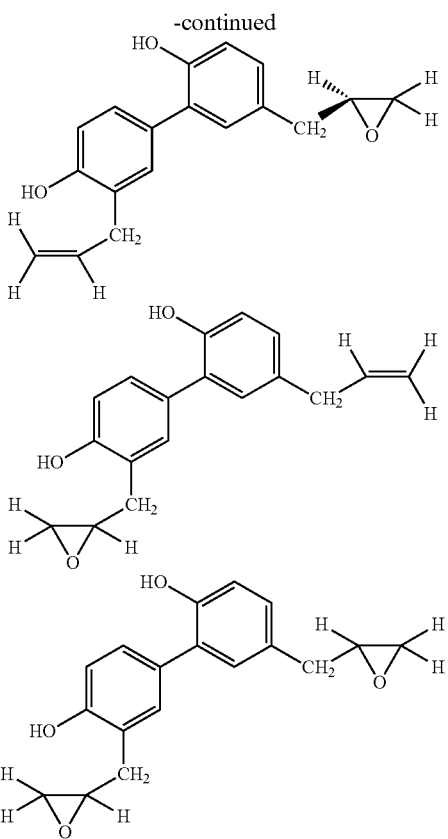

The compounds shown above have a double bond that can be present in either cis or trans (E or Z) form, and also a chiral carbon on the epoxide ring, which can be in either the R or S configuration, or mixtures thereof. The individual compounds representing the various stereoisomeric forms and isomeric forms of these compounds are within the scope of the invention.

The compounds of any of the above formulas can be present in the form of racemic mixtures or pure enantiomers, or occur in varying degrees of enantiomeric excess, and racemic mixtures can be purified using known chiral separation techniques.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

II. Methods of Preparing the Compounds

The compounds of Formula I have a bi-aryl, aryl-heteroaryl, or bi-heteroaryl core structure, where each ring includes a hydroxyl group and a side chain. Depending on the definition of W, the side chain can include an ether, thioether, or amine bridge between the aryl/heteroaryl ring and the three membered ring. Depending on the definition of X, the three membered ring can be a cyclopropane, epoxide, thiirane, or aziridine.

Generally, methods for producing bi-aryl, aryl-heteroaryl, or bi-heteroaryl core structures are known, and involve coupling chemistry between an aryl halide and an aryl organometallic compound, such as an aryl lithium or aryl zinc halide. Hydroxy groups present in appropriate positions on the aryl/heteroaryl rings can be protected during the coupling chemistry using known protecting groups.

Ideally, the aryl/heteroaryl rings either include an appropriate side chain or side chain precursor, or include appropriate functionality to attach the side chain. A double bond can serve as a precursor for a cyclopropane, epoxide, thiirane, or aziridine ring, as discussed in more detail below.

Accordingly, using known starting materials, one can couple two appropriately substituted aryl rings, an aryl ring and a heteroaryl ring, or two heteroaryl rings, attach a side chain or side chain precursor, if the side chain or side chain precursor is not already attached, and convert one or more side chain precursors (i.e., double bonds) into cyclopropane, epoxide, thiirane, or aziridine rings. Representative processes for effecting these conversions are described in detail below.

Synthesis of Honokiol Analogues Using Honokiol as a Starting Material

Honokiol can be used as a starting material for certain honokiol analogues, principally those in which the modification to honokiol is the conversion of one or both of the double bonds to a cyclopropane, epoxide, thiirane, or aziridine ring. The chemistry for converting the double bonds to these rings is discussed in more detail below.

Synthesis of Bi-Phenyls, Phenyl-Heteroaryl, and Bi-Heteroaryl Rings

Biaryl, aryl-heteroaryl, and bi-heteroaryl rings can be prepared, for example, using the Negishi coupling reaction. This reaction involves the nickel- or palladium-catalyzed coupling of organozinc compounds with various halides (aryl and heteroaryl halides). For example, 2-bromo-pyridine can be reacted with t-butyl lithium to produce the lithio salt, and this lithio salt reacted with zinc chloride to produce the 2-zinc chloride salt. This zinc chloride salt can be coupled, for example, with 2-chloropyridine to produce a bi-pyridine (i.e., a 2,2'-bipyridine).

The Negishi coupling reaction involves formation of organometallic salts, and any hydroxyl groups present in the aryl/heteroaryl ring will be deprotonated unless they are protected with suitable protecting groups. Further, any dichloroacetate and alkyl phosphate ester analogues of these hydroxyl groups will likely be reacted with the organometallic salts, so it is best to prepare any dichloroacetate and alkyl phosphate ester analogues after the Negishi coupling step.

Biphenyl rings can typically be prepared by reacting fluoroaryl rings with an aryl lithium compound. The reaction is believed to proceed by a benzyne intermediate.

Compounds where W is $C_{1-4}$ Alkyl or Haloalkyl

Compounds where W is $C_{1-4}$ alkyl or haloalkyl, such as perfluoroalkyl or any fluorinated analogue with from one fluorine to perfluorination, can be prepared via a number of methods, including either a) having an appropriate $C_{1-4}$ alkyl moiety, with a double bond attached at the terminal end of the side chain, present during the coupling of the aryl/heteroaryl rings to form the biaryl, aryl-heteroaryl, or bi-heteroaryl rings, or b) including a functional group on the aryl/heteroaryl rings that can be converted to a $C_{1-4}$ alkyl moiety, with a double bond attached at the terminal end of the side chain.

For example, if a halide is present on one of the aryl/heteroaryl rings, it can be reacted, for example, using conventional coupling chemistry, with a halo-alkene (such as an allyl halide (also known as a 3-halo-prop-1-ene, for example, allyl bromide), 4-halo-but-1-ene, 5-halo-pent-1-ene, or 6-halo-hex-1-ene), to form an aryl-alkene or heteroaryl-alkene intermediate. Following the coupling reaction, the double bond can be converted to a suitable three membered ring, such as a cyclopropane, epoxide, thiirane, or aziridine. The double bond-containing moieties listed above would produce a three membered ring with a ($CH_2$) moiety, but if other functionalization is desired, one of the hydrogens on the $=CH_2$ terminus of the halo-alkene could be replaced with an alkyl, aryl, alkylaryl, or arylalkyl group. Such double bond-containing materials are either well known to those of skill in the art, or can be easily prepared using conventional chemistry.

If one or more double bond-containing moieties are present during the coupling of the aryl/heteroaryl rings, they will not interfere with nor be destroyed during the coupling chemistry. Similarly, if a cyclopropane ring-containing side chain is present on the aryl/heteroaryl ring during the coupling chemistry, the ring will not be adversely affected during the coupling chemistry. However, if a side chain when X O, S, or $NR^2$ were present during the coupling chemistry, these groups might be adversely affected, so it is preferred to first provide the double bond moiety, and then to convert it to the desired cyclopropane, thiirane, or aziridine moiety.

Compounds where W is O—$(CHR^2)n$, S—$(CHR^2)n$, or $NR^2$—$(CHR^2)n$

Compounds where W is O—$(CHR^2)n$, S—$(CHR^2)n$, or $NR^2$—$(CHR^2)n$ can be prepared via a number of methods, including either a) having an appropriate O—$(CHR^2)_n$, S—$(CHR^2)n$, or $NR^2$—$(CHR^2)n$ alkyl moiety, with a double bond attached at the terminal end of the side chain, present during the coupling of the aryl/heteroaryl rings to form the biaryl, aryl-heteroaryl, or bi-heteroaryl rings, or b) including a protected hydroxyl, thiol, or amine group on the aryl/heteroaryl rings that can be deprotected and subsequently converted to an O—$(CHR^2)n$, S—$(CHR^2)n$, or $NR^2$—$(CHR^2)n$ moiety, with a double bond attached at the terminal end of the side chain. The latter can be accomplished, for example, by reaction of a hydroxyl, thiol, or amine with an alkenyl bromide (as above) to form an ether, thioether, or amine linkage.

In some embodiments, it is desired to incorporate halogens, such as flourines, into the alkyl group (i.e., $(CF_2)n$). Such fluorinated moieties can readily be incorporated, using techniques known to those of skill in the art.

Conversion of Double Bonds to Cyclopropane Rings

Following the attachment of double bond-containing side chains, one or both of the double bonds can be converted to cyclopropane rings. The cyclopropane rings can include a $CH_2$ moiety, or can be substituted with one or two methyl groups.

The derivatives described herein include derivatives in which one or both of the double bonds is replaced with a (unsubstituted, monoalkyl or dialkyl, where alkyl can be substituted or unsubstituted, and is preferably methyl)cyclopropyl group.

The synthesis of alkyl, such as methyl, dialkyl, such as dimethyl and unsubstituted cyclopropane derivatives is well known to those of skill in the art, and involves, for example, bromoform reaction to form the dibromocyclopropane derivative, followed by stoichiometric reaction with a hydride or an alkyl-lithium. An aryl-lithium will provide aryl substitution on the cyclopropane ring. If fluoro-substitution is desired on the cyclopropane ring, it can be provided, for example, by displacing the bromines with fluorines using known chemistry.

Conversion of Double Bonds to Epoxide Rings

Following the attachment of double bond-containing side chains, one or both of the double bonds can be converted to epoxide rings. The epoxide rings can be formed, for example, by reaction of the double bond with m-chloroperbenzoic acid. Alternatively, the epoxide rings can be formed by halohydrogenation of the double bond to form halohydrins, followed by the addition of base. Halohydrins are typically prepared by adding aqueous hypochlorous acid (HOCl) or hypobromous acid (HOBr) to alkenes, often by using aqueous solutions of the halogen, where the reaction proceeds by formation of the intermediate halonium ion. The base deprotonates the hydroxyl group, which then nucleophilically displaces the halide to form the epoxide ring. The choice of reaction conditions can be made depending on the susceptibility of the other substituents on the intermediate to such reaction conditions.

Conversion of Double Bonds to Thiirane Rings

Following the attachment of double bond-containing side chains, one or both of the double bonds can be converted to thiirane rings. The thiirane rings can be formed, for example, by bromination of the double bond, followed by S'-substitution in sodium sulfides (see for example, Choi J et al (1995) Bull. Korean. Chem. Soc., 16, 189-190, Convenient Synthesis of Symmetrical Sulfides from Alkyl Halides and Epoxides).

Conversion of Double Bonds to Aziridine Rings

Following the attachment of double bond-containing side chains, one or both of the double bonds can be converted to aziridine rings. The aziridine rings can be formed, for example, by selective aziridination of olefins with p-toluenesulfonamide catalyzed by dirhodium(II) caprolactamate. Aziridine formation occurs through aminobromination and subsequent base-induced ring closure. See, for example, A. J. Catino, J. M. Nichols, R. E. Forslund, M. P. Doyle, Org. Lett., 2005, 7, 2787-2790.

Protection and Deprotection of Hydroxy Groups

As discussed herein, hydroxyl groups present on the aryl/heteroaryl rings may need to be protected during portions of the synthesis, and deprotected at a later time. Protecting groups, and methods for their removal, are well known to those of skill in the art, and are described for example, in T. W. Greene and P. G. M. Wuts, Protective Groups in Organic Synthesis, $3^{rd}$ Edition, John Wiley & Sons, New York (1999).

Conversion of Hydroxy Groups to Phosphate Esters

One or both of the hydroxyl groups present on the aryl/heteroaryl rings, on honokiol itself or on a honokiol analogue, can be converted to phosphate esters (i.e., where R1 is a phosphate ester moiety), including alkyl phosphates, by reacting the hydroxyl group(s) with a phosphorylating agent, such as phosphoric anhydride, polyphosphoric acid, phosphorous oxychloride, and phosphorous pentoxide.

Conversion of Hydroxy Groups to Dichloroacetate or Valproic Acid Esters

One or both of the hydroxyl groups present on the aryl/heteroaryl rings, on honokiol itself or on a honokiol analogue, can be converted to dichloroacetate and/or valproic acid esters (i.e., where R1 is a dichloroacetate moiety, $Cl_2CHC(O)$— or a valproate moiety), by reacting the hydroxyl group(s) with dichloroacetic acid, valproic acid, an activated forms thereof. The dichloroacetic acid or valproic acid can be coupled to a hydroxyl group directly, with an acid catalyst and subsequent formation of water (typically removed by azeotropic distillation), or by reaction with an acid halide or anhydride form of dichloroacetic acid or valproic acid, typically in the presence of a tertiary amine such as triethylamine.

Conversion of Hydroxy Groups to Trifluoromethyl Ethers

Starting with honokiol or the analogues thereof, one can readily convert one or both of the hydroxyl groups to a trifluoromethyl ether, using techniques known to those of skill in the art. For example, an alkoxide salt of honokiol or an analogue thereof can be reacted with trifluoroiodomethane to form the trifluoromethyl ether.

The starting materials used to make the honokiol analogues described herein are either commercially available, or can be prepared from commercially available starting materials. Those that are not commercially available can be made by a variety of synthetic methodologies, related to the particular moieties and the particular substitution desired. The variation in synthetic methodology will be readily apparent to those of skill in the art of organic synthesis.

Those skilled in the art will readily understand that incorporation of other substituents onto the aromatic or heteroaromatic rings used as a starting material to prepare the honokiol analogues, and other positions in the honokiol framework, can be readily realized. Such substituents can provide useful properties in and of themselves or serve as a handle for further synthetic elaboration.

Substituents typically can be added to a phenyl ring, heteroaryl ring, bi-phenyl moiety, phenyl-heteroaryl and/or bi-heteroaryl moiety before adding the side chains.

A number of other analogs, bearing substituents in the diazotized position of the aryl/heteroaryl rings, can be synthesized from the corresponding amino compounds, via diazonium salt intermediates. The diazonium salt intermediates can be prepared using known chemistry, for example, as described above.

Nitration of an aryl or heteroaryl results, followed by reaction with a nitrite salt, typically in the presence of an acid, produces an amine functionality on the aryl/heteroaryl ring. Other substituted analogs can be produced from diazonium salt intermediates, including, but are not limited to, hydroxy, alkoxy, fluoro, chloro, iodo, cyano, and mercapto, using general techniques known to those of skill in the art. For example, hydroxy-aryl/heteroaryl analogues can be prepared by reacting the diazonium salt intermediate with water. Likewise, alkoxy honokiol analogues can be made by reacting the diazonium salt with alcohols. The diazonium salt intermediates can also be used to synthesize cyano or halo compounds, as will be known to those skilled in the art. Mercapto substitutions can be obtained using techniques described in Hoffman et al., J. Med. Chem. 36: 953 (1993). The mercaptan so generated can, in turn, be converted to an alkylthio substitutent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, Org. React. (N.Y.) 42: 335 (1992) and Hughes, Org. Prep. Proced. Int. 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings (and pyridine, pyrimidine, pyrazine, and other heteroaryl rings) can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene ring.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more of the honokiol analogues described herein, and/or pharmaceutically acceptable salts thereof. Optically active compounds can be employed as racemic mixtures, as pure enantiomers, or as compounds of varying enantiomeric purity.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

The compounds can be incorporated into drug delivery devices such as nanoparticles, microparticles, microcapsules, and the like. Representative microparticles/nanoparticles include those prepared with cyclodextrins, such as pegylated cyclodextrins, liposomes, including small unilamellar vesicles, and liposomes of a size designed to lodge in capillary beds around growing tumors. Suitable drug delivery devices are described, for example, in Heidel J D, et al., Administration in non-human primates of escalating intravenous doses of targeted nanoparticles containing ribonucleotide reductase subunit M2 siRNA, Proc Natl Acad Sci USA. 2007 Apr. 3; 104(14):5715-21; Wongmekiat et al., Preparation of drug nanoparticles by co-grinding with cyclodextrin: formation mechanism and factors affecting nanoparticle formation, Chem Pharm Bull (Tokyo). 2007 March; 55(3):359-63; Bartlett and Davis, Physicochemical and biological characterization of targeted, nucleic acid-containing nanoparticles, Bioconjug Chem. 2007 March-April; 18(2): 456-68; Villalonga et al., Amperometric biosensor for xanthine with supramolecular architecture, Chem Commun (Camb). 2007 Mar. 7; (9):942-4; Defaye et al., Pharmaceutical use of cyclodextrines: perspectives for drug targeting and control of membrane interactions, Ann Pharm Fr. 2007 January; 65(1):33-49; Wang et al., Synthesis of Oligo(ethylenediamino)-beta-Cyclodextrin Modified Gold Nanoparticle as a DNA Concentrator; Mol Pharm. 2007 March-April; 4(2): 189-98; Xia et al., Controlled synthesis of Y-junction polyaniline nanorods and nanotubes using in situ self-assembly of magnetic nanoparticles, J Nanosci Nanotechnol., 2006 December; 6(12):3950-4; and Nijhuis et al., Room-temperature single-electron tunneling in dendrimer-stabilized gold nanoparticles anchored at a molecular printboard, Small. 2006 December; 2(12):1422-6.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where cancer cells are located. The compounds described herein are very potent at treating these cancers.

In certain circumstances, the compounds described herein can be employed as part of a pharmaceutical composition with other compounds intended to prevent or treat a particular cancer, i.e., combination therapy. In addition to effective amounts of the compounds described herein, the pharmaceutical compositions can also include various other components as additives or adjuncts.

Combination Therapy

The combination therapy may be administered as (a) a single pharmaceutical composition which comprises a honokiol analogue as described herein, at least one additional pharmaceutical agent described herein, and a pharmaceutically acceptable excipient, diluent, or carrier; or (b) two separate pharmaceutical compositions comprising (i) a first composition comprising a honokiol analogue as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, the honokiol analogues described herein can be administered together with at least one other chemotherapeutic agent as part of a unitary pharmaceutical composition. Alternatively, the honokiol analogues can be administered apart from the other anticancer chemotherapeutic agent. In this embodiment, the honokiol analogues and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering a honokiol analogue, as described herein, or a pharmaceutically acceptable salt or prodrug of a compound described herein, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anticancer compounds that can be used in combination with the honokiol analogues are described below.

The honokiol analogues can be combined with alpha-1-adrenoceptor antagonists, such as doxazosin, terazosin, and tamsulosin, which can inhibit the growth of prostate cancer cell via induction of apoptosis (Kyprianou, N., et al., Cancer Res 60:4550 4555, (2000)).

Sigma-2 receptors are expressed in high densities in a variety of tumor cell types (Vilner, B. J., et al., Cancer Res. 55: 408 413 (1995)) and sigma-2 receptor agonists, such as CB-64D, CB-184 and haloperidol, activate a novel apoptotic pathway and potentiate antineoplastic drugs in breast tumor cell lines. (Kyprianou, N., et al., Cancer Res. 62:313 322 (2002)). Accordingly, the honokiol analogues can be combined with at least one known sigma-2 receptor agonists, or a pharmaceutically acceptable salt of said agent.

The honokiol analogues can be combined with lovastatin, a HMG-CoA reductase inhibitor, and butyrate, an inducer of apoptosis in the Lewis lung carcinoma model in mice, can potentiate antitumor effects (Giermasz, A., et al., Int. J. Cancer 97:746 750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225 232 (2002)). Accordingly (in addition to forming honokiol analogues of these compounds), the honokiol analogues can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145 150 (1999)). 4HPR also was reported to have good activity in combination with gamma-radiation on bladder cancer cell lines (Zou, C., et al., Int. J. Oncol. 13:1037 1041 (1998)). Representative retinoids and synthetic retinoids include, but are not limited to, bexarotene, tretinoin, 13-cis-retinoic acid, 9-cis-retinoic acid, .alpha.-difluoromethylornithine, ILX23-7553, fenretinide, and N-4-carboxyphenyl retinamide.

Proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433 443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472 1478 (2002)). Representative tyrosine kinase inhibitors include, but are not limited to, Gleevec®, ZD1839 (Iressa®), SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544 3550 (2001)). Synergy of the protein farnesyltransferase inhibitor SCH66336 and cisplatin in human cancer cell lines also has been reported (Adjei, A. A., et al., Clin. Cancer. Res. 7:1438 1445 (2001)). Prenyl-protein transferase inhibitors, including farnesyl protein transferase inhibitor, inhibitors of geranylgeranyl-protein transferase type I (GGPTase-I) and geranylgeranyl-protein transferase type-II, or a pharmaceutically acceptable salt of said agent, can be used in combination with the honokiol analogues described herein. Examples of known prenylprotein transferase inhibitors include, but are not limited to, R115777, SCH66336, L-778,123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209 4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Hunting) 16 (No. 4 Suppl. 3):17 21 (2002)). Representative COX-2 inhibitors include, but are not limited to, celecoxib, valecoxib, and rofecoxib.

Any of the above-mentioned compounds can be used in combination therapy with the honokiol analogues. Additionally, many of these compounds can be converted to honokiol analogues by reaction of ketone, aldehyde, hydroxyl, thiol, and/or amine functional groups on the compounds using the chemistry described herein. The honokiol analogues of these compounds are within the scope of this invention.

Further, the honokiol analogues can be targeted to a tumor site by conjugation with therapeutically useful antibodies, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates can also enhance the anticancer effect of therapeutically useful antibodies, such as Herceptin® or Rituxan®.

The compounds can also be used in conjunction with surgical tumor removal, by administering the compounds before and/or after surgery, and in conjunction with radiation therapy, by administering the compounds before, during, and/or after radiation therapy.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the honokiol analogue is an amount sufficient to suppress the growth of the tumor(s), and, ideally, is a sufficient amount to shrink the tumor, and, more ideally, to destroy the tumor. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 .mu.g/24 hr/patient. The effective dose generally does not exceed about 500, often does not exceed about 400, and frequently does not exceed about 300 .mu.g/24 hr/patient. In addition, administration of the effective dose is such that the concentration of the compound within the plasma of the patient normally does not exceed 500 ng/mL and frequently does not exceed 100 ng/mL.

IV. Methods of Using the Compounds and/or Pharmaceutical Compositions

The compounds described herein, and pharmaceutical compositions including the compounds, can be used to treat cancers. Representative disorders that can be treated include neoplasms, such as hemangiomas, and malignant tumors, for example, those which arise in the setting of autocrine loops involving vascular endothelial growth factor (VEGF) and its major mitogenic receptor vascular endothelial growth factor receptor 2. Representative malignant tumors include malignant endothelial tumors such as melanoma. Additional cancers that can be treated include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease, and malignant forms of these cancers.

In some embodiments, the patient already has cancer and is undergoing treatment for the cancer, and may or may not have tumor metastasis (i.e., secondary cancer).

The cancer may be manifested in the form of a tumor, such as a tumor of epithelial tissue, lymphoid tissue, connective tissue, bone, or central nervous system.

The compounds can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Treatment of Osteoporosis

The honokiol analogues can also be used to treat osteoporosis. The cytokine RANKL (receptor activator of NF-.kappa.B ligand) causes osteoporosis by activating osteoclasts. Honokiol is known to inhibit RANKL activity by potentiating apoptosis, suppresses osteoclastogenesis, and inhibits invasion through modulation of nuclear factor-kappaB activation pathway (see, for example, Mol Cancer Res. 2006 September; 4(9):621-33). The honokiol analogues treat osteoporosis via the same mechanism.

Treatment of Inflammatory Disorders

The honokiol analogues described herein are useful for treating or preventing inflammatory disorders. Reactive oxygen drives NFkB in inflammatory disorders such as rheumatoid arthritis, asthma, psoriasis, eczema, lupus, scleroderma, certain heart diseases such atherosclerosis and coronary artery disease, and the like. Because the honokiol analogues are effective at inhibiting production of reactive oxygen species, they are active against inflammatory disorders.

The honokiol analogues also inhibit certain inflammatory signals, and can alleviate inflammatory disorders such as inflammatory arthritis by inhibiting these signals. For example, CD40 and its Epstein Barr viral mimic, LMP1, have been implicated in exacerbation of chronic autoimmune disease, and the honokiol analogues inhibit CD40 and LMP1 inflammatory signaling mechanisms. The effectiveness of the analogues at treating inflammatory disorders can be shown by their ability to stabilize the severity of symptomatic collagen-induced arthritis in both CD40-LMP1 transgenic mice and their congenic C57Bl/6 counterparts. The anti-inflammatory effects of these compounds can also be measured, for example, in mouse B cell lines expressing the hCD40-LMP1 chimeric receptor, by measuring CD40 and LMP1-mediated NFkB and AP-1 activation, and the concomitant decrease in TNF-.alpha. and IL-6. The anti-inflammatory properties of these honokiol analogues can be used to block the autoimmune response.

Rheumatoid arthritis (RA) is considered the most common systemic autoimmune disease, but other disorders, such as hypothyroidism, systemic lupus erythematosus (SLE), and the like can also be treated using the honokiol analogues. A number of conditions are associated with chronic inflammation and elevated levels of TNF-.alpha. and IL-6, including rheumatoid arthritis, heart disease, and cancer.

Numerous gastrointestinal disorders are caused by inflammation, including, but not limited to, Chrohn's disease, irritable bowel syndrome, and inflammatory bowel syndrome, and these disorders can also be treated and/or prevented using the compounds described herein.

There is a suggested link between rheumatoid arthritis and chronic inflammation due to the re-activation of Epstein-Barr virus (EBV), which latently infects a proportion of memory B cells in >90% of the world's population. Among the EBV-encoded proteins implicated in viral pathogenesis, considerable attention has focused upon latent membrane protein 1 (LMP1). Of the nine EBV genes expressed as proteins in EBV-transformed cells, LMP1 is the best characterized, and is the only EBV-encoded gene product capable of transforming cells in vitro and in vivo, resulting in the potential for lymphoproliferative changes and malignancy. In addition to its established role in the pathogenesis of B cell lymphoma and other malignancies, EBV infection may be linked to exacerbation of various human autoimmune diseases, including RA and SLE.

The mouse collagen-induced arthritis (CIA) model (Myers, et al., Life Science 61: 1861-1878 (1997)) has many pathologic and immunologic parallels to rheumatoid arthritis, and provides a stable, predictable model for evaluating the therapeutic potential of compounds for treating chronic inflammatory conditions. This model can be used, for example, to evaluate the ability of the honokiol analogues to treat and/or prevent these disorders.

Treatment of mouse B cell lines with the honokiol analogues in vitro can be shown to recapitulate the cytokine profile seen in primary mouse B cells with a concomitant dose-dependent decrease in CD40 and LMP 1-mediated NFkB and AP-1 activation. Those compounds which decrease CD40 and LMP1-mediated NFkB and AP-1 activation in a dose-dependent manner will be expected to have anti-inflammatory properties, potentially in both the cognitive phase of the immune response, as well as the effector phase, by inhibiting cytokines that lead to chronic inflammation and additional pathology.

Treatment of Ocular Disorders

The compounds are also suitable for use in treating ocular disorders with an inflammatory component, such as macular degeneration, retinal vasculitis, uveitis, conjunctivitis, episcleritis, scleritis, optic neuritis, retrobulbar neuritis, ocular inflammation following ocular surgery, and ocular inflammation resulting from physical eye trauma. In this embodiment, the compounds can be delivered via eye drops or other suitable topical formulation for direct administration to the eye.

Treatment of Neurodegenerative Disorders and/or Providing Neuroprotection

Reactive oxygen species also induce inflammation and neurodegeneration. Inhibition of these species can also result in neuroprotection, including protection from further damage following an ischemic brain injury such as a stroke, or that caused from blunt trauma, and treatment or prevention of neurodegenerative disorders such as Alzheimer's disease, senile dementia, pre-senile dementia, Parkinsons disease, Huntington's Chorea, multiple sclerosis, and the like.

Reactive oxygen species also drive seizures, and the honokiol analogues have GABAergic activity which may ameliorate seizures as well.

The following examples are provided to illustrate the present invention, and should not be construed as limiting thereof. In these examples, all parts and percentages are by weight, unless otherwise noted. Reaction yields are reported in mole percentages.

EXAMPLES

The following examples are provided to illustrate the present invention and should not be construed as limiting the scope thereof. In these examples, all parts and percentages are by weight, unless otherwise noted. Reaction yields are reported in mole percentage.

Example 1

Spectrophotometric Assay of NADH Oxidase

NADH oxidase activity can be determined as the disappearance of NADH measured at 340 nm in a reaction mixture containing 25 mM Tris-Mes buffer (pH 7.2), 1 mM KCN, and 150 .mu.M NADH at 37.degree. C. Activity can be measured, for example, using a Hitachi U3210 spectrophotometer with stifling and continuous recording over two intervals of 5 min each. A millimolar extinction coefficient of 6.22 can be used to determine specific activity.

Example 2

Measuring Cell Growth

A mouse mammary tumor subpopulation line 4T1 arising from a BALB/cf C3H mouse can be grown in DME-10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 .mu.g/ml) (Miller et al., 1987, Brit. J. Can. 56:561-569 and Miller et al., 1990, Invasion Metastasis 10:101-112).

Example 3

In Vitro Testing of Various Test Compounds

Nude mice were injected subcutaneously with approximately one million tumor cells. Once tumors became visible, they were treated with 40 mg/kg daily of honokiol diepoxide. The compound was reconstituted in 100 microliters of ethanol and diluted with 900 microliters of 20% Intralipid, and 0.3 ml of this mixture was injected intraperitoneally daily. Tumors were measured with vernier calipers, and tumor volume was calculated using the formula (width$^2$.times.length) 0.52, where width is the smallest dimension, 2 represents squared, and 1 represents the length.

The results are shown in Table 1, below, and in FIG. 1.
TABLE-US-00001 TABLE 1 Tumor Volume in Honokiol Diepoxide-Treated Animals Group L W Tumor Volume Average Control Honokiol Epoxide Control 12.42 10.18 669.2994922 21.82 21.24 5118.787665 22.58 11.98 1685.159129 2491.082 2491.082 433.3632 Honokiol 0 0 0 Epoxide 10.04 8.59 385.2329125 14.54 11 914.8568 433.3632

TABLE 1

| | Tumor Volume in Honokiol Diepoxide-Treated Animals | | | | | |
|---|---|---|---|---|---|---|
| Group | L | W | Tumor Volume | Average | Control | Honokiol Epoxide |
| Control | 12.42 | 10.18 | 669.2994922 | | | |
| | 21.82 | 21.24 | 5118.787665 | | | |
| | 22.58 | 11.98 | 1685.159129 | 2491.082 | 2491.082 | 433.3632 |
| Honokiol | 0 | 0 | 0 | | | |
| Epoxide | 10.04 | 8.59 | 385.2329125 | | | |
| | 14.54 | 11 | 914.8568 | 433.3632 | | |

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention claimed is:

1. A compound selected from the group consisting of valproate mono and diesters of honokiol, dichloroacetate mono and diesters of honokiol, and $C_{1-6}$ alkyl phosphate mono and di-esters of honokiol.

2. A compound of the formula:

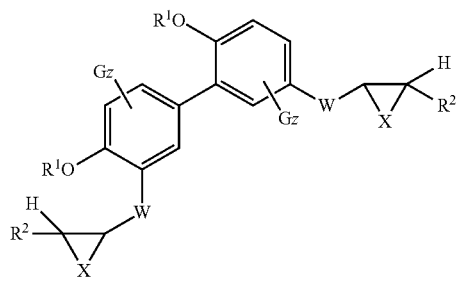

wherein:
W is $(CHR^2)n$, wherein the $(CHR^2)n$ portion of the W moiety can be fluorinated with anywhere from one fluorine atom to complete perflourination, X is O or $CR^2$,
$R^1$ is H, $C_{1-8}$ alkyl phosphate, or dichloroacetate, with the proviso that at least one of $R^1$ is dichloroacetate;
$R^2$ is H, $C_{1-8}$ alkyl, phenyl, phenyl-$C_{1-8}$alkyl, or $C_{1-8}$alkyl-phenyl, and, when bonded to carbon, can be halo, n is an integer from 1-4,
G is selected from the group consisting of $C_{1-6}$ alkyl, $C_{2-8}$ alkenyl, phenyl, halo, —$OR^1$, —$NR^3R^4$, —$CF_3$, —CN, —$NO_2$, —$C_2R^3$, —$SR^3$, —$N_3$, —C(=O)$NR^3R^4$, —$NR^3C$(=O)$R^3$, —C(=O)$R^3$, —C(=O)$R^3$, —OC(=O)$R^3$, —OC(=O)$NR^3R^4$, —$NR^3CO$(=O)$R^3$, —$SO_2R^3$, —$SO_2NR^3R^4$, and —$NR^3SO_2R^3$, where $R^3$ and $R^4$ are individually hydrogen, $C_{1-6}$ alkyl, $C_{3-8}$ cycloalkyl, phenyl, or phenyl-$C_{1-8}$ alkyl,
z is an integer of from 0-3, but in any case cannot exceed the number of carbon atoms in the ring, and one of the three membered rings can be replaced with a double bond.

3. A compound of claim 2, wherein both of X are O.

4. A compound of claim 2, wherein one of X is O, and the other represents a bond between the two carbons to which it is attached.

5. A compound of claim 2, wherein each $R^2$ is H.

6. A compound of claim 2, wherein each W is $CH_2$.

7. A compound of claim 2, wherein two of $R^1$ represent a dichloroacetate.

8. A method for treating a cancer in a mammal, comprising administering to the mammal a therapeutically effective amount of a compound of claim 1 in an amount sufficient to induce apoptosis and/or inhibit angiogenesis, such that the growth of the tumor is at least partially inhibited, wherein the cancer is selected from a group consisting of hemangioma, melanoma, rectal carcinoma, colon carcinoma, breast carcinoma, ovarian carcinoma, small cell lung carcinoma, colon carcinoma, chronic lymphocytic carcinoma, hairy cell leukemia, osophogeal carcinoma, prostate carcinoma, breast cancer, myeloma, and lymphoma, or wherein the tumor is a tumor of epithelial tissue, lymphoid tissue, connective tissue, bone, or the central nervous system.

9. The method of claim 8, wherein the cancer is a metastasized cancer.

10. The method of claim 8 wherein the human is immunosuppressed by reason of having undergone anti-cancer therapy prior to administration of the composition.

11. The method of claim 8, wherein the compounds are administered parenterally, orally, directly into the tumor, via an implanted device, or using a sustained release formulation.

12. A method of treating inflammatory disorders, comprising administering a compound of claim 1 to a patient in need of treatment thereof, wherein the inflammatory disorder is selected from the group consisting of, rheumatoid arthritis, asthma, psoriasis, eczema, lupus, scleroderma, atherosclerosis, and coronary artery disease.

13. A compound selected from the group consisting of honokiol mono-dichloroacetate and honokiol bis-dichloroacetate.

* * * * *